United States Patent [19]

Singer et al.

[11] 4,276,211

[45] Jun. 30, 1981

[54] STABILIZATION COMPOSITION FOR COATING COMPOSITION

[75] Inventors: William Singer, Teaneck; Milton Nowak, South Orange; Norma Ingles, Edison, all of N.J.

[73] Assignee: Troy Chemical Corporation, Newark, N.J.

[21] Appl. No.: 129,058

[22] Filed: Mar. 10, 1980

[51] Int. Cl.$^3$ .......................... C08L 23/00; C09D 5/14
[52] U.S. Cl. ........................ 260/29.6 MN; 106/18.32; 106/18.35; 260/45.8 A; 260/45.9 NC; 424/150
[58] Field of Search ................ 260/29.6 MN, 45.8 A, 260/45.9 NC; 106/18.32, 18.35; 424/150; 528/119, 405

[56] References Cited

U.S. PATENT DOCUMENTS 3,923,870  12/1975  Singer .............................. 260/482 C Primary Examiner—Hosea E. Taylor
Assistant Examiner—Amelia B. Yarbrough
Attorney, Agent, or Firm—E. Janet Berry

[57] ABSTRACT

The invention comprises a method for the color stabilization of iodoalkyne carbamates by the addition thereto of selected epoxy compounds. The epoxy compounds which thus function as stabilizers may be employed as a part of solutions containing the iodoalkyl carbamates, or they may be employed as a part of the films, coatings or compositions containing the iodoalkyne compounding.

22 Claims, No Drawings

STABILIZATION COMPOSITION FOR COATING COMPOSITION

The invention generally concerns stabilization of certain products which have been found useful for their fungicidal activity in paints, coatings and the like.

It is an object of this invention to provide stabilized compositions of urethanes prepared from halogen substituted lower molecular weight alkynes.

It is another object of the invention to prepare color stabilized urethane compounds which show high level fungicidal activity in coating compositions.

It is another object to use epoxy compounds as color stabilizers for urethane fungicides.

Another object is to provide color stabilized compositions which are a mixture containing at least a urethane derived from halogen substituted lower molecular alkynes and epoxy compounds.

Other and further objects of the invention will be apparent from the detailed description presented below.

Urethane compounds which are derivatives of 1-halogen substituted lower molecular weight alkynes having the formula

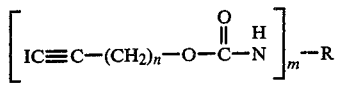

wherein R is a substituted or unsubstituted alkyl, aryl, or alkylaryl group having from one to not more than 20 carbon atoms and having from one to three linkages corresponding to m, and m and n are whole number integers between 1 and 3 and may be the same or different. These compounds have been found to have great fungicidal activity. They are particularly useful in surface coating compositions such as paint formulations.

These compounds have found great success commercially for fungicidal protection in all kinds of coating and surface protective compositions.

For example, the compound 3-iodopropynyl N-butyl carbamate has found wide commercial acceptance and is used to protect paint film, wood, adhesives, and similar products from fungal attack.

One serious disadvantage has been found to the use of these materials as fungicides and this disadvantage limits severely wider applications. A serious degree of color instability is caused by the presence of these materials. This becomes evident on storage of solutions containing this compound for extended periods of time, especially during storage in warm climates. In such instances, the color of the solution, which is initially light turns gradually to a dark, unacceptable amber or dark reddish yellow. Moreover, this yellowing of the solution will occasionally carry over into the systems into which it is incorporated. This type of discoloration is particularly objectionable in systems where clean white colors are desirable, such as in white bathroom caulks, white paints, paper coatings, plastics coatings, and the like.

For instance, and as a further disadvantage, this color instability caused by the presence of these fungicides often becomes evident in connection with white surfaces, such as paints, which are exposed to strong light, particularly sunlight. It is interesting to observe that aggravation of this tendency to become yellow in sunlight occurs even when the sunlight passes through a pane of window glass, which will screen out much of the ultra-violet. Ordinary diffuse light, other than direct sunlight, appears however to have little or no effect.

In addition to the tendency of the solution of the carbamate fungicide to discolor or darken in color upon standing, the additive also frequently causes yellowing of the dried paint films in which it may be incorporated. This tendency toward yellowing of the dried paint film may vary somewhat with the composition of the paint and with its formulation. Usually, however, all paints containing these urethane compositions exhibit a tendency to at least some degree for causing yellowing of their dried paint films.

Since a large market for these urethanes as fungicides is in white paint whose ultimate use is intended for the exterior of homes, a study was made to determine some of the formulation factors which might be involved in this discoloration phenomenon. By testing a series of paints identical to each other except for one component, some typical ingredients were found to increase this tendency to yellow more than others. For example, alkalis, such as ammonia, ammonium hydroxide, alkaline metal hydroxides such as sodium hydroxide, amines such as mono-ethanolamine, morpholine, alkaline metal carbonates, including the widely used calcium carbonate pigments, and organic compounds containing double bonds, including unsaturated oils and alkyd resins which are frequently incorporated into latex paints, were all studied for their effects.

From these tests there was selected a typical paint formulation that exhibited moderate to severe yellowing characteristics when a standard solution of 40% iodopropynyl butyl carbamate was added to it.

A paint formulation was designed that would include many of these aggravating factors, and which would be suitable for testing purposes. This paint formulation is not an atypical one and there are many commercial compositions that are similar to it. It is to be understood that the tests performed with this paint do not yield absolute values, but only comparative ones. Other paint compositions having similar formulations would yield the same sort of data, but to a lesser or greater degree. What this means is that any compound showing color stabilizing activity in this paint would show more or less similar effects when used in other paint compositions.

It has now been discovered that a group of compounds containing the epoxy group function very effectively as stabilizers of solutions of the group of urethane compounds described for instance in U.S. Pat. No. 3,923,870, or in films of compositions containing them.

The use of epoxy compounds as co-stabilizers for chlorine containing compounds has been previously known. For example, epichlorohydrin has been recommended as a stabilizer for chlorinated rubber, and epoxidized oils are useful when combined with the well-known barium-cadmium soaps for polyvinyl chloride. The use of stabilizers for iodine containing compounds such as the herein identified iodine containing urethanes is totally unknown since iodine is a relatively expensive element. It is not often used where the less expensive chlorine will do. Moreover, iodinated alkanes are known for the ease with which they can be dehalogenated. Thus the ease of dehalogenation occurs in the order: iodine>bromine>chlorine>fluorine. Thus, polyvinyl iodide would be extremely unstable in a practical sense since it is so easily hydrolyzed or dehalogenated. An iodine atom attached to a triple bond carbon atom, on the other hand, is removed only with the utmost difficulty, requiring special conditions and the use of strong reagents. Thus compounds which would function as stabilizers for polyvinyl chloride, chlorinated rubber and the like would not necessarily be useful for iodoalkyne carbamates. This effect is shown in the various detailed examples set forth hereinbelow.

The urethane compounds are most conveniently prepared by (1) iodinating the appropriate acetylenic alcohol, then (2) carrying out a subsequent reaction with an isocyanate to form the corresponding urethane. These reactions may be represented to proceed typically as follows:

Step (1):
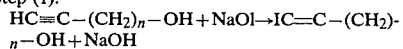
$HC{\equiv}C-(CH_2)_n-OH + NaOI \rightarrow IC{\equiv}C-(CH_2)_n-OH + NaOH$ Step (2): $IC{\equiv}C-(CH_2)_n-OH + R[NCO]_m \longrightarrow$

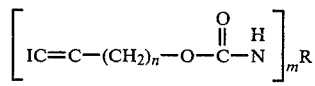
$$\left[ IC{\equiv}C-(CH_2)_n-O-\overset{\overset{O}{\|}}{C}-\overset{H}{N} \right]_m R$$

In these formulas and equations, R, n and m have the following meanings:

R is a radical selected from the group consisting of substituted and unsubstituted alkyl, aryl and alkylaryl groups having from one to not more than 20 carbon atoms and having from one to three linkages corresponding to m, and m and n are whole number integers between 1 and 3 and may be the same or different.

If desired, the urethane compounds may be purified using a suitable solvent and recovery.

For use as a fungicide, however, complete purification of the urethanes is not necessary. Some of the products are solids and some are liquids, frequently oils. Haloacetylene compounds are somewhat unstable, and the products obtained may contain some decomposition or secondary reaction products. These do not detract from their fungicidal efficacy, but such impurities do make difficult the obtaining of very precise physical constants. However, analytical tests have yielded results consistent with the indicated structures.

It is in no way intended to limit the preparation of the compounds to the exact process or steps above described. Any equivalent procedure which yields the same end products may of course be used.

These urethane compounds have shown a number of advantages over those heretofore available as fungicides. The urethanes are excellent fungicides. The urethanes are excellent fungicides in all types of paints. They are hydrolytically stable and may be used in both latex and oil based systems. They are soluble in many solvents and may therefore readily be diluted for convenience or ease of use. Their compatibility, low color, and efficiency make them advantageous for use as fungicides in plastics, and for impregnation into wood, leather, paper, cloth or other materials.

Tests indicate a degree of toxicity and skin irritation far below that of mercurials, a fact that widens their area of usefulness.

The urethanes may be applied on or incorporated into compositions that must withstand attack by a varied fungus population. These compounds are extremely potent against the three major fungal organisms: *aspergillus niger, pullularia pullulans,* and alternaria sp., and are comparable therefore to mercurials in their effectiveness against a wide range of fungi.

These compounds may, of course, be applied to surfaces in various ways—incorporated into a coating or composition, applied as a dust by mixing with powdered diluents, dissolved in a solvent, emulsified into water, and dispersed into a non-solvent. The particular application desired will generally dictate the method of use.

The percentage of active compound necessary to achieve the desired result will vary somewhat depending on the compound used, the substrate to be protected, the conditions for fungal growth, and the amount of protection desired. However, the concentrations generally range from 0.01% up to 4% in the composition applied. When R is $C_6$ or lower grouping the usual levels of usage range between 0.05 and 2%.

Set forth below are the general testing procedures used in determining the effectiveness of the epoxy compounds for heat stabilization of the carbamates.

I. FOR SOLUTIONS

A stock solution of 3-iodo-2-propynl N-butyl carbamate is made by dissolving 40 G of the compound in 40 G dipropylene gylcol and 20 G of diacetone alcohol. To aliquots of this solution there are added the various compounds to be tested as stabilizers at a level of 5%, unless otherwise indicated. They are filled into Gardner-Holdt color tubes and placed in a constant temperature chamber which is held at a temperature of 125° F. Color readings are taken periodically. The scale runs from 0 to 18, with 0 being colorless and 18 a very dark amber.

II. FOR PAINTS

A paint was prepared from the following formulation

A paste was prepared by grinding the following ingredients in a paint mill:
500 G water
1.5 G potassium carbonate
24 G anionic dispersant (25% low ml. wt. sodium polyacrylate)
300 G titanium dioxide
900 G calcium carbonate
150 G asbestine
3 G preservative (hydroxymethyl-amino ethanol)
6 G defoamer After the above paste was ground smooth there was added:
1425 G acrylic copolymer (Rhoplex AC388-Rohm & Haas) 47% solids
210 G polyester (long oil soya-linseed alkyd)
15 G non-ionic emulsifier (nonyl phenol plus 10 moles ethylene oxide)

A further addition was made of a pre-mix of the following ingredients:
3 G 28% ammonia
225 G water
225 G 2½% hydróxyethyl cellulose solution-grade 4400 plus additional ammonia as required to bring the pH at least above 9.

In carrying out the actual testing procedures, to 1840 G of this test paint there was added 27.6 G (1.5%) of the stock (40% active) solution prepared as described in I above. The compounds to be tested as film stabilizers were made up as 20% solutions in either propylene glycol or ethylene glycol monoethyl ether as required. Various amounts of these 20% solutions corresponding to 10% of the compound under test, based on the 40% active fungicidal solution were added to 80 G aliquots of the test paints. These were mixed thoroughly and aged in a constant temperature chamber held at 125° F. for approximately one week. The samples were then removed, allowed to cool for one hour, and 3 mil films from them applied to coated paper panels with a suitable applicator. After being permitted to dry for 1 hour indoors, the coated panels were placed outdoors, facing into direct sunlight. The samples were visibly observed at time intervals for discoloration or yellowing. The ratings scale used for evaluation is shown below:
1 = White—no discoloration
2 = Faint Yellow—not objectionable
3 = Light Yellow
4 = Moderate Yellowing—objectionable
5 = Dark Yellow—very objectionable These ratings, though somewhat subjective, are completely valid for paint discoloration effects. Numerical values obtained by means of a reflectometer for example are found not to be reproducible, since here are so many unavoidable variables involved such as sun intensity, temperature, and the like.

EXAMPLE 1

The following tests were conducted using Procedure I for preparing the solutions which were tested for color stability.

| Test No. | Stabilizer | Initial Color | Final Color | Days Exposed (Days Later) |
|---|---|---|---|---|
| Series I (tested at 5% conc.) | | | | |
| 1 | None | 12–13 | 18 | (23) |
| 2 | Epichlorohydrin | 12–13 | 14 | (23) |
| 3 | Styrene Oxide | 12–13 | 14 | (23) |
| 4 | Glycidyl Methacrylate | 12–13 | 14 | (23) |
| 5 | Allyl Glycidyl Ether | 12–13 | 15 | (23) |
| 6 | Formic Acid | 12–13 | over 18 | (23) |
| Series 2 (tested at 5% conc.) | | | | |
| 7 | None | 12 | over 18 | (20) |
| 8 | Epichlorohydrin | 12 | 12 | (20) |
| 9 | Epoxidized Oil | 12 | 15 | (20) |
| 10 | Triphenyl Phosphite | 12 | over 18 | (20) |
| 11 | Proprietary Commercial Vinyl Stabilizer (Mark-C-Witco) | 12 | over 18 | (15) |
| 12 | Proprietary Commercial Vinyl Stabilizer (Nuostatie V-2019-Tenneco) | 12 | over 18 | (15) |
| 13 | Proprietary Epoxy Resins: | | | |
| 14 | Araldite 8047 (Ciba) | 12 | 12–13 | (30) |
| 15 | Araldite 6060 (Ciba) | 12 | 14 | (30) |
| 16 | Araldite 6004 (Ciba) | 12 | 13 | (30) |
| 17 | Araldite CY-179 (Ciba) | 12 | 14 | (30) |
| 18 | ERE 1359 (Ciba) | 12 | 12–13 | (30) |
| 19 | Diphenyl Phosphite | 12 | over 18 | (1) |
| 20 | Isooctyl diphenyl phosphite | 12 | over 18 | (1) |
| 21 | Trilauryl tin thiophosphite | 12 | incompatible | |
| 22 | Butyrolactone | 12 | 16 | (9) |
| 23 | Tributyl tin oxide | 12 | 17 | (9) |
| Series 3 (tested at 5% conc.) | | | | |
| 24 | None | 12 | 15 | (10) |
| 25 | Cyclohexene oxide | 11 | 13 | (14) |
| 26 | Vinyl Cyclohexene Dioxide | 11 | 12–13 | (14) |
| 27 | 1,2 Epoxybutane | 11 | 12 | (14) |
| 28 | 2,3 Epoxy-propyl P-methoxy phenyl ether | 11 | 12 | (14) |
| 29 | Araldite 8047 (Ciba) | 11 | 12 | (14) |
| 30 | Dipropylene glycol monomethyl ether | 12 | 15 | (10) |
| 31 | β-methyl delta valerolactone | 12 | 16 | (10) |
| 32 | 6 Acetoxy-2,4 dimethyl m-dioxane | 12 | 16–17 | (10) |
| 33 | Trioctyl phosphate | 12 | 15 | (10) |
| 34 | Octyl Epoxy tallate | 12 | 14–15 | (10) |
| 35 | 4,5 epoxytetrahydrophthalate | 12 | 14 | (10) |
| 36 | diisodecyl 4,5 epoxy tetrahydrophthalate | 11 | 14 | (10) |
| 37 | 2-pyrrolidone | 12 | 16 | (10) |
| 38 | n-methyl 2-pyrrolidone | 12 | 15 | (10) |
| 39 | butanediol diglycidyl ether | 12–13 | 13 | (10) |
| 40 | Calcium octoate/5% | 11–12 | 15 | (6) |
| 41 | Dibutyl tin bis isooctyl thioglycolate | 12 | 18 | (4 hrs.) |
| 42 | 1,2 epoxy, 3-phenoxy-propane | 12 | 12–13 | (10) |
| Series 4 (tested at 5% conc.) | | | | |
| 43 | None | 13 | 13 | (14) |
| 44 | Epoxy RD-1 (Ciba) | 12–13 | 15 | (14) |
| 45 | EPN1139 (Ciba) | 12–13 | 15 | (14) |
| 46 | CY 183 (Ciba) | 12–13 | 15 | (14) |
| 47 | Hydrazine Hydrate (85%) | 12–13 | over 18 | (4) |
| 48 | Cadmium neodecanoate (16.5%) | 12–13 | over 18 | (10) |
| 49 | Barium neodecanoate (16.4%) | 12–13 | 17–18 | (14) |

-continued

| Series 5 | | | Conc. 5% | | Conc. 2% |
|---|---|---|---|---|---|
| 50 | None | 9 | over 18 | (25) | over 18 |
| 51 | Butyrolactone | 9 | over 18 | (12) | over 18 |
| 52 | Epichlorohydrin | 9 | 16–17 | (35) | 16 |
| 53 | Propylene Oxide | 9 | 14 | (35) | 18 |
| 54 | Trichlorobutylene oxide | 9 | 16 | (35) | 18 |

These data clearly demonstrate that the conventional vinyl stabilizers, with the exception of epoxy compounds, do not provide color stabilization of these iodo compounds. The outstanding stabilization seen by comparing the color ratings of Test 7 with those of Tests 10, 11, 12, 19, 20 and 21; also results from test 24 with those of 41 and 42; also results from Test 43 with those of 48 and 49.

It has thus been clearly shown that the epoxy compounds as a class have a marked and unexpected color stabilizing effect on solutions of the fungicidally active carbamate compounds.

It is highly significant and unusual that other compounds which have been tested either show a negative or no effect at all in color stabilization of these solutions.

EXAMPLE 2

The following tests were conducted using Procedure II for preparing paint films which were tested for light stability.

| Stabilizer | Numerical Rating After Aging Fourteen (14) Days in 125° F. Chamber |
|---|---|
| Negative control (no Cpd) | 1 |
| Epichlorohydrin | 2 |
| Epoxy EPN-1139 (Ciba) | 3 |
| CY-183 (Ciba) | 3 |
| Propylene Glycol | 3 |
| Epoxy 6004 (Ciba) | 4 |
| RD-1 (Ciba) | 4 |
| 2,3 Epoxy propyl p-methoxyphenyl ether | 4 |
| 1,2 Epoxy 3 phenoxypropane | 4 |
| Trichlorbutylene oxide | 4 |
| Araldite CY-179 (Ciba) | 5 |
| ERE-1359 (Ciba) | 5 |
| Epoxy 8047 (Ciba) | 5 |
| Epoxy 506 (Ciba) | 5 |
| Positive control - no stabilizer | 5 - Darkest of all |

In this Example 2, many of the epoxy compounds which were found as shown in Example 1 to stabilize the color of solutions of the carbamate compounds were also tested in paint films. All epoxy compounds showed some activity; however, some of them are more effective in retarding discoloration than are others.

The data presented in the above examples show the effectiveness of epoxy compounds in retarding discoloration or yellowing of carbamate solutions. This class of epoxy compounds is also found to be effective in slowing down or decreasing light promoted discoloration of films or surfaces containing fungicidally effective levels of the iodoalkyne carbamates which are generally used in concentrations of under 5%, although more or less amounts can be employed.

It is understood that the solvents used in making up solutions of the iodoalkyne carbamates may vary, depending on the requirements for the end use as coatings or in coating compositions. Thus, it has been clearly shown that epoxy compounds are effective color stabilizers for these solutions, and may be used in varying concentrations such as 2, 5, 25, and 60%. Indeed, those organic epoxy compounds which are normally liquid can be used as the sole solvent or carrier of the active iodo carbamate component. These may be very valuable in protecting polyvinyl chloride film from fungal attack. In addition, compounding of coating compositions may include a variety of such well known components as emulsifying agents, pigments, wetting agents, and the like, such thickeners, anti-settling agents as may be required to provide for effective, stable emulsions when added to water or aqueous systems. These components and compounding procedures are well known to commercial operations. Thus, the essential feature of this invention is the discovery of color stabilization by the presence of the organic epoxy compounds.

EXAMPLE 3

Solutions were made of several other carbamates made from hydroxyiodo propyne and mono or polyisocyanates, at varying concentrations, with and without epoxy compound RD-1 (butyl glycidyl ether) to indicate that stabilization is not limited to 3-iodo-2 propynyl N-butyl carbamate.

| | | Series 6 | | | |
|---|---|---|---|---|---|
| No. | Isocyanate Used in Prep. | Concentration | Solvent | % RD-1 | Initial Color | Color after 5 Days at 125° F. |
| 55 | Cyclohexanone | 14.3% | Cellosolve | — | 1 | 6 |
| 56 | Cyclohexanone | 14.3% | Cellosolve | 10 | 1 | 1 |
| 57 | Ethyl | 40% | Carbitol-DMS(4:1) | — | 8 | 10 |
| 58 | Ethyl | 40% | Carbitol-DMS(4:1) | 10 | 7 | 8 |
| 59 | 1,6 Diisocyanatohexane | 14.3% | Carbitol-DMS(4:1) | — | 4 | 9 |
| 60 | 1,6 Diisocyanatohexane | 14.3% | Carbitol-DMS(4:1) | 10 | 4 | 3 |
| 61 | 2,4 Diisocyanatotoluene | 14.3% | Carbitol-DMS(4:1) | — | 13 | 18 |
| 62 | 2,4 Diisocyanatotoluene | 14.3% | Carbitol-DMS(4:1) | 10 | 9 | 12 |
| 63 | Phenyl | 33.3% | Carbitol- | — | 7 | 10 |

-continued

Series 6

| No. | Isocyanate Used in Prep. | Concentration | Solvent | % RD-1 | Initial Color | Color after 5 Days at 125° F. |
|---|---|---|---|---|---|---|
| 64 | Phenyl | 33.3% | DMS(4:1) Carbitol-DMS(4:1) | 10 | 7 | 7 |
| 65 | Hexyl | 20% | Carbitol-DMS(4:1) | — | 11 | 13 |
| 66 | Hexyl | 20% | Carbitol-DMS(4:1) | 10 | 11 | 12 |

Cellosolve - ethylene glycol monoethyl ether
Carbitol - diathylene glycol monoethyl ether
DMS - dimethyl sulfoxide An examination of the above data indicates the usefulness of epoxy compounds in retarding or decreasing color degradation of compositions containing iodoalkynylcarbamates, when iodine is on the end triple bond carbon.

What is claimed is:

1. A composition adapted for use in coating applications which contains at least one iodo compound having the formula:

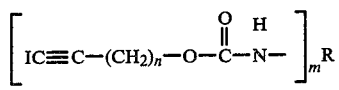

in which R is an alkyl, aryl, alkaryl, alkene, cyclohexyl or similar group having one to not more than 20 carbon atoms and having from one to three linkages corresponding to m and n and m are whole number integers between 1 and 3 and may be the same or different, and at least one organic epoxy compound.

2. The composition of claim 1 in which the iodo compound has the formula of claim 1 in which m is 1.

3. The compound of claim 1 in which the iodo compound has the formula of claim 1 in which m is 2.

4. A composition adapted for use in coating applications which contains the butyl urethane of 3 hydroxy-1-iodopropyne and an organic epoxy compound.

5. A composition adapted for use in coating applications which contains the t-butyl urethane of 3 hydroxy-1-iodopropyne and an organic epoxy compound.

6. A composition adapted for use in coating applications which contains the hexyl urethane of 3 hydroxy-1-iodopropyne and an organic epoxy compound.

7. A composition adapted for use in coating applications which contains the methyl urethane of 3-hydroxy-1-iodopropyne and an organic epoxy compound.

8. A coating composition containing an iodo compound having the formula:

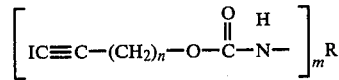

in which R is an alkyl, aryl or alkaryl, alkene, cyclohexyl or similar group having one to not more than 20 carbon atoms and having from one to three linkages corresponding to m and n and m are whole number integers between 1 and 3 and may be the same or different, and at least one organic epoxy compound.

9. The coating composition of claim 8 in which the iodo compound has the formula of claim 8 in which m is 1.

10. The coating compound of claim 8 in which the iodo compound has the formula of claim 8 in which m is 2.

11. A coating composition adapted for use in coating applications which contains the butyl urethane of 3 hydroxy-1-iodopropyne and an organic epoxy compound.

12. A coating composition adapted for use in coating applications which contains the t-butyl urethane of 3 hydroxy-1-iodopropyne and an organic epoxy compound.

13. A coating composition adapted for use in coating applications which contains the hexyl urethane of 3-hydroxy-1-iodopropyne and an organic epoxy compound.

14. A coating composition adapted for use in coating applications which contains the methyl urethane of 3-hydroxy-1-iodopropyne and an organic epoxy compound.

15. A paint containing an iodo compound as a fungicide having the formula:

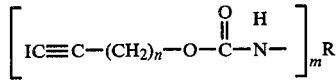

in which R is an alkyl, aryl or alkaryl, alkene, cyclohexyl or similar group having one to not more than 20 carbon atoms and having from one to three linkages corresponding to m and n and m are whole number integers between 1 and 3 and may be the same or different and at least one organic expoxy compound.

16. The paint of claim 15 in which the iodo compound has the formula of claim 15 in which m is 1.

17. The paint of claim 15 in which the iodo compound has the formula of claim 15 in which m is 2.

18. A paint containing an iodo compound as a fungicide which contains the butyl urethane of 3 hydroxy-1-iodopropyne and an organic epoxy compound.

19. A paint containing an iodo compound as a fungicide which contains the t-butyl urethane of 3 hydroxy-1-iodopropyne and an organic epoxy compound.

20. A paint containing an iodo compound as a fungicide which contains the hexyl urethane of 3-hydroxy-1-iodopropyne and an organic epoxy compound.

21. A paint containing an iodo compound as a fungicide which contains the methyl urethane of 3-hydroxy-1-iodopropyne and an organic epoxy compound.

22. The method for color stabilization of coating compositions containing iodo-carbamates which comprises incorporating therein small but effective amounts of organic epoxy compounds.

* * * * *